(12) United States Patent
Sartor et al.

(10) Patent No.: US 9,539,018 B2
(45) Date of Patent: Jan. 10, 2017

(54) DEVICES, SYSTEMS, AND METHODS FOR TISSUE MORCELLATION

(71) Applicant: COVIDIEN LP, Mansfield, MA (US)

(72) Inventors: Joe D. Sartor, Longmont, CO (US); John G. Westwood, San Jose, CA (US); Aaron D. Leyva, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 233 days.

(21) Appl. No.: 14/325,590

(22) Filed: Jul. 8, 2014

(65) Prior Publication Data

US 2015/0018837 A1 Jan. 15, 2015

Related U.S. Application Data

(60) Provisional application No. 61/882,714, filed on Sep. 26, 2013, provisional application No. 61/845,188, filed on Jul. 11, 2013.

(51) Int. Cl.
*A61B 17/24* (2006.01)
*A61B 17/32* (2006.01)
(Continued)

(52) U.S. Cl.
CPC ..... *A61B 17/32002* (2013.01); *A61B 17/3205* (2013.01); *A61B 17/32053* (2013.01);
(Continued)

(58) Field of Classification Search
CPC .......... A61B 17/320016; A61B 17/32002; A61B 17/3205; A61B 17/32053; A61B 2017/320024; A61B 2017/320028; A61B 2017/320032; A61B 2017/00455; A61B 2017/293; A61B 2017/320775; A61B 18/1445

See application file for complete search history.

(56) References Cited

U.S. PATENT DOCUMENTS

| 5,403,276 A | 4/1995 | Schechter et al. |
| 5,443,472 A | 8/1995 | Li |

(Continued)

FOREIGN PATENT DOCUMENTS

| EP | 806183 A1 | 11/1997 |
| GB | 2327350 A | 1/1999 |

(Continued)

OTHER PUBLICATIONS

U.S. Appl. No. 14/325,550.

*Primary Examiner* — Robert Lynch

(57) ABSTRACT

A morcellation system includes a morcellator and a grasper. The morcellator includes a housing and a tube extending from the housing and having at least one blade section. The morcellator further includes an oscillating mechanism configured to oscillate the tube. An end cap is coupled to the proximal end of the housing and is configured to receive the tube. The end cap defines a passage and includes an aligning structure disposed in the passage. The grasper includes a tubular member having a grasping end including first and second jaws moveable relative to one another. The grasper further includes a handle assembly operatively associated with the grasping end. A keyed collar is disposed about the tubular member. The keyed collar includes a key configured to cooperate with the aligning structure of the end cap to align the first and second jaws relative to the distal end of the tube.

15 Claims, 6 Drawing Sheets

(51) Int. Cl.
  *A61B 18/14* (2006.01)
  *A61B 17/3205* (2006.01)
  *A61B 18/00* (2006.01)

(52) U.S. Cl.
  CPC .. *A61B 18/1482* (2013.01); *A61B 17/320016* (2013.01); *A61B 18/1445* (2013.01); *A61B 2017/320024* (2013.01); *A61B 2018/00208* (2013.01); *A61B 2018/00601* (2013.01)

(56) References Cited

U.S. PATENT DOCUMENTS

| | | | |
|---|---|---|---|
| 5,520,634 A | 5/1996 | Fox et al. | |
| 5,569,284 A | 10/1996 | Young et al. | |
| 5,618,296 A | 4/1997 | Sorensen et al. | |
| 5,669,927 A | 9/1997 | Boebel et al. | |
| 5,746,760 A | 5/1998 | Humphrey, Jr. | |
| 5,916,198 A * | 6/1999 | Dillow | A61B 17/3498 604/167.04 |
| 6,039,748 A | 3/2000 | Savage et al. | |
| 6,045,566 A | 4/2000 | Pagedas | |
| 6,162,235 A | 12/2000 | Vaitekunas | |
| 6,468,228 B1 | 10/2002 | Topel et al. | |
| D535,748 S | 1/2007 | Wolf | |
| 7,156,839 B2 | 1/2007 | Bayer et al. | |
| 7,232,439 B2 | 6/2007 | Ciarrocca | |
| 7,850,684 B2 | 12/2010 | Marshall et al. | |
| 8,025,656 B2 | 9/2011 | Gruber et al. | |
| 8,100,928 B2 | 1/2012 | Nohilly et al. | |
| 8,152,820 B2 | 4/2012 | Mohamed et al. | |
| 8,308,746 B2 | 11/2012 | Pravong et al. | |
| 8,343,148 B2 | 1/2013 | Fleming et al. | |
| 8,608,764 B2 | 12/2013 | Ambardekar | |
| 8,652,156 B2 | 2/2014 | Holdgate et al. | |
| 2005/0261676 A1 | 11/2005 | Hall et al. | |
| 2006/0089527 A1* | 4/2006 | Doll | A61B 1/31 600/105 |
| 2008/0039880 A1 | 2/2008 | Nohilly et al. | |
| 2008/0039883 A1 | 2/2008 | Nohilly | |
| 2008/0058846 A1 | 3/2008 | Vosough | |
| 2008/0065129 A1 | 3/2008 | Batchelor et al. | |
| 2008/0103412 A1 | 5/2008 | Chin | |
| 2008/0135780 A1 | 6/2008 | Giering et al. | |
| 2008/0255597 A1* | 10/2008 | Pravong | A61B 17/32002 606/169 |
| 2009/0292281 A1* | 11/2009 | Fleming | A61B 18/1445 606/48 |
| 2010/0305566 A1 | 12/2010 | Rosenblatt et al. | |
| 2011/0184409 A1 | 7/2011 | Jenkins et al. | |
| 2011/0257651 A1 | 10/2011 | Jenkins | |
| 2011/0264129 A1* | 10/2011 | Holdgate | A61B 17/3462 606/170 |
| 2012/0016399 A1 | 1/2012 | Poulsen | |
| 2012/0078038 A1 | 3/2012 | Sahney et al. | |
| 2013/0090642 A1 | 4/2013 | Shadduck et al. | |
| 2013/0123797 A1 | 5/2013 | Livneh | |
| 2013/0218186 A1 | 8/2013 | Dubois et al. | |

FOREIGN PATENT DOCUMENTS

| | | |
|---|---|---|
| GB | 2327351 A | 1/1999 |
| WO | 2009141579 A1 | 11/2009 |
| WO | 2014/123571 A1 | 8/2014 |

\* cited by examiner

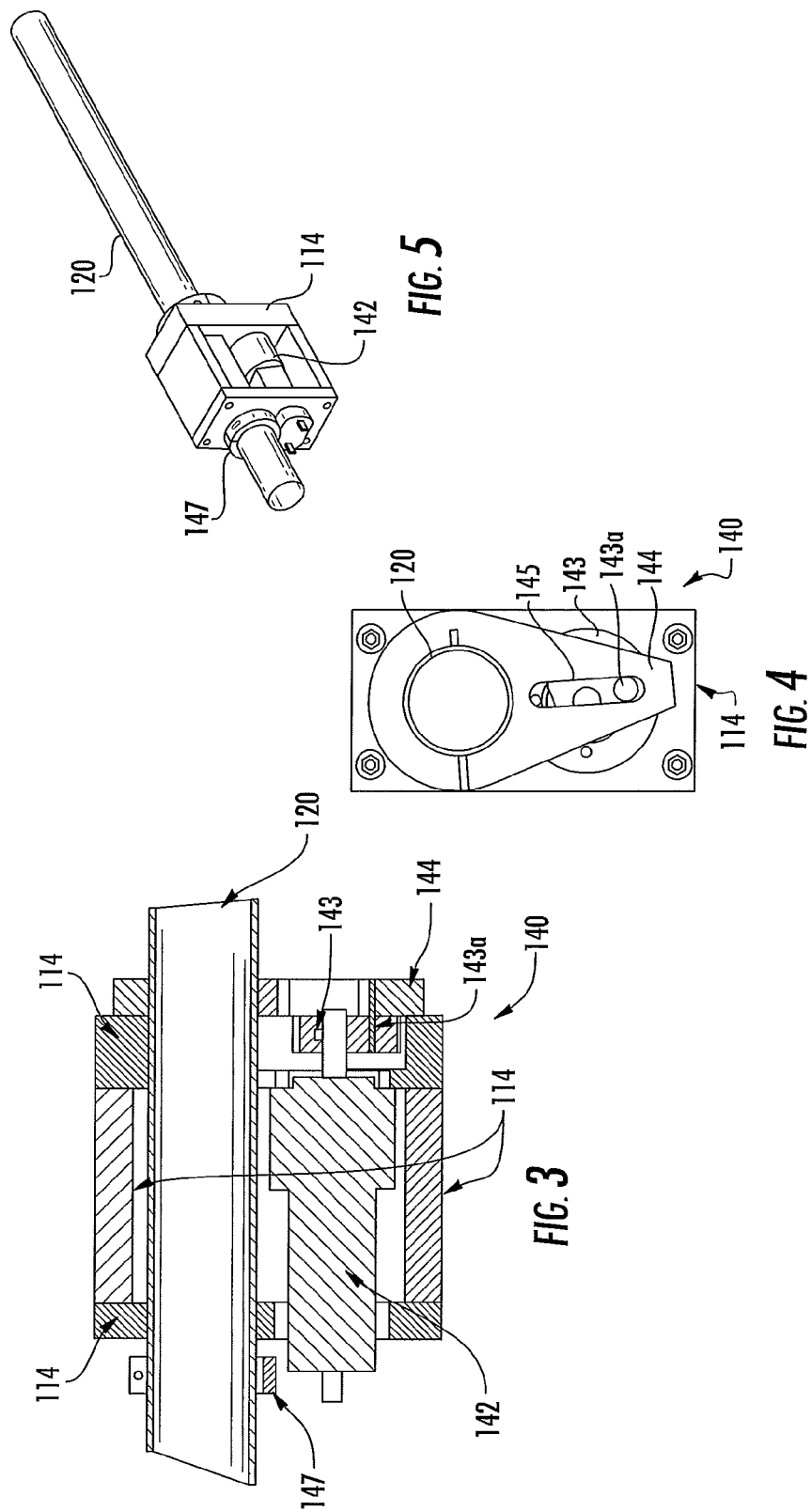

DEVICES, SYSTEMS, AND METHODS FOR TISSUE MORCELLATION

CROSS-REFERENCE TO RELATED APPLICATIONS

This application claims the benefit of, and priority to, U.S. Provisional Patent Application Ser. Nos. 61/845,188, which was filed on Jul. 11, 2013, and 61/882,714, which was filed on Sep. 26, 2013. This application is related to U.S. patent application Ser. No. 14/325,550, filed on Jul. 8, 2014. The entire contents of each of the above applications are hereby incorporated herein by reference.

BACKGROUND

1. Technical Field

The present disclosure relates to tissue morcellation and, more specifically, to minimally invasive tissue morcellators, morcellation systems, and tissue morcellation methods, which can be used for partial or total removal of body tissue or organs.

2. Description of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue-piercing instrument such as a trocar, or by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. myomectomy, nephrectomy, cholecystectomy, lobectomy, and other procedures including thoracic, abdominal, laparoscopic, and endoscopic procedures. During such procedures, it is common that a cyst, fibroid, myoma, tumor, or other affected tissue or organ needs to be removed via the access opening or through a cannula. Various types of entrapment devices have been disclosed to facilitate this procedure. In many procedures where cancerous tumors are removed, removal of the specimen in an enclosed environment is highly desirable to inhibit seeding of cancer cells (i.e., portions of cancer cells contacting healthy tissue).

Several minimally invasive surgical procedures require the bulk removal of body tissue or organs through a limited surgical opening. As such, the tissue needs to be morcellated within the body cavity into smaller pieces of tissue to facilitate removal with laparoscopic graspers or tenaculums through minimally invasive access ports or the morcellation tool itself. Examples of such tissue morcellation are found in myomectomies, laparoscopic nephrectomies, splenectomies, or laparoscopic supracervical hysterectomies.

In laparoscopic cases for bulk removal of tissue, it is advantageous to morcellate the tissue into large tissue segments, rather than small tissue breakups, which then can be removed in very few extraction steps. Apart from time savings, the removal of large tissue segments, rather than small tissue chips, also reduces the chance of cross-contamination with malignant or cancerous tissue. Specifically for the example of laparoscopic supra-cervical hysterectomies, it is advantageous to morcellate the severed uterus along the surface of the fundus (generating a continuous tissue peel), rather than to repetitively core into the bulk of the uterus (generating a multitude of tissue chips).

During morcellation, the opened jaws of the grasper or tenaculum may damage the edge of the cutting blade during manipulation, dramatically reducing its effectiveness and life.

SUMMARY

In aspects of the present disclosure, a morcellation system includes a morcellator and a grasper. The morcellator includes a housing, an elongated tube, an oscillating mechanism, and an end cap. The elongated tube extends distally from the housing, defines a longitudinal axis, and defines a lumen therethrough. A distal end of the elongated tube includes one or more blade sections that are configured to cut tissue. The blade sections may be disposed at an angle relative to a plane orthogonal to the longitudinal axis. The oscillating mechanism is configured to oscillate the elongated tube about the longitudinal axis. The end cap is coupled to the proximal end of the housing and is configured to receive a proximal end of the elongated tube. The end cap defines a passage disposed about the longitudinal axis of the elongated tube. The passage includes an aligning structure.

The grasper includes a tubular member, a grasping end, a handle assembly, and a keyed collar. The tubular member includes proximal and distal ends. The grasping end is positioned adjacent the distal end of the tubular member and includes first and second jaws moveable relative to one another. The handle assembly is positioned adjacent the proximal end of the tubular member and is operatively associated with the grasping end. The keyed collar is disposed about the tubular member between the proximal and distal ends thereof. The keyed collar includes a key configured to cooperate with the aligning structure of the end cap to align the first and second jaws relative to the distal end of the elongated tube, e.g., with desired sections of the distal end of the elongated tube.

In aspects of the present disclosure, the oscillating mechanism is configured to mechanically drive the elongated tube to oscillate. The oscillating mechanism can include a motor, a disc shaped cam, and a connecting member. The cam includes a distally extending cam pin affixed near the outer circumference of the cam. The connecting member includes a cam slot that is configured to receive the cam pin. The connecting member is fixed to the outer surface of the elongated tube and is configured to translate the rotation of the motor into oscillation of the elongated tube about the longitudinal axis.

In aspects of the present disclosure, the oscillating mechanism is configured to electromagnetically drive the elongated tube to oscillate. The oscillating mechanism can include one or more magnets affixed to the elongated tube and one or more corresponding solenoids. The solenoid(s) is configured to oscillate the elongated tube by generating magnetic fields that act upon the magnet(s).

In aspects of the present disclosure, the aligning structure is a keyway and the key protrudes from the outer surface of the collar. The key may be configured to be received within the keyway. In some embodiments, the keyway includes a first section, a second section, and a third section. The first section tapers distally from a first dimension to a second dimension smaller than the first dimension. The second section has a substantially constant dimension equal to the second dimension. The third section tapers distally from the second dimension to a third dimension greater than the second dimension. In other aspects of the present disclosure, the aligning structure is a pair of cap magnets and the key is a pair of collar magnets.

In aspects of the present disclosure, a method of morcellating tissue includes inserting a distal end of a morcellator into a surgical site, inserting a grasping end of a grasper through the morcellator, aligning first and second jaws of the grasping end relative to the distal end of the morcellator, feeding tissue to be morcellated to the distal end of the morcellator with the grasping end of the grasper, and activating the morcellator to morcellate tissue.

In aspects, activating the morcellator may include oscillating a distal cutting end of an elongated tube of the morcellator to morcellate tissue. Oscillating the distal cutting end may include mechanically driving the elongated tube to oscillate. In some embodiments, oscillating the distal cutting end includes electromagnetically driving the elongated tube to oscillate. In aspects, aligning the first and second jaws of the grasping end includes inserting the collar disposed about a tubular member of the grasper into the end cap of the morcellator such that the key cooperates with the aligning structure to align the grasper.

In aspects of the present disclosure, a surgical kit includes a morcellator, a specimen retrieval apparatus, a grasper, and a keyed collar. The morcellator, grasper and/or keyed collar may be similar to any of those detailed above.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 1A is a side view of the distal end of the morcellator of FIG. 1;

FIG. 3 is a cross-sectional view of the internal components of the housing of the morcellator of FIG. 1;

FIG. 4 is a front view of the morcellator of FIG. 1 with the housing removed;

FIG. 5 is a rear perspective view of the morcellator of FIG. 1 with the housing removed;

DETAILED DESCRIPTION

Figure 1:
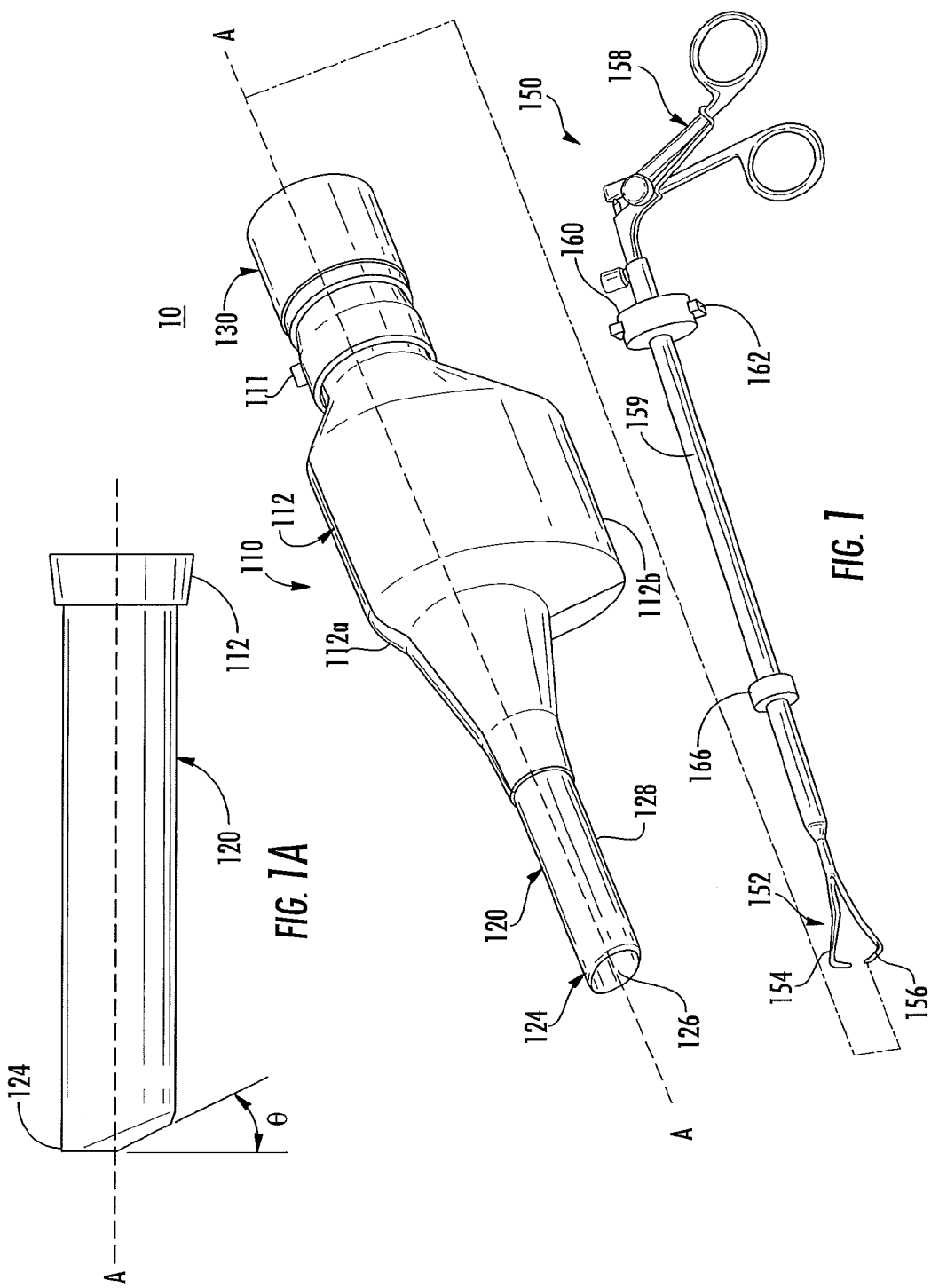
FIG. 1 is a front perspective view of an exemplary embodiment of a morcellation system in accordance with the present disclosure including a morcellator and a grasper.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is furthest from the clinician.

Referring to FIG. 1, an exemplary embodiment of a morcellation system 10 provided in accordance with the present disclosure incorporates an oscillating morcellator 110 and a tenaculum or grasper 150.

Figure 2:
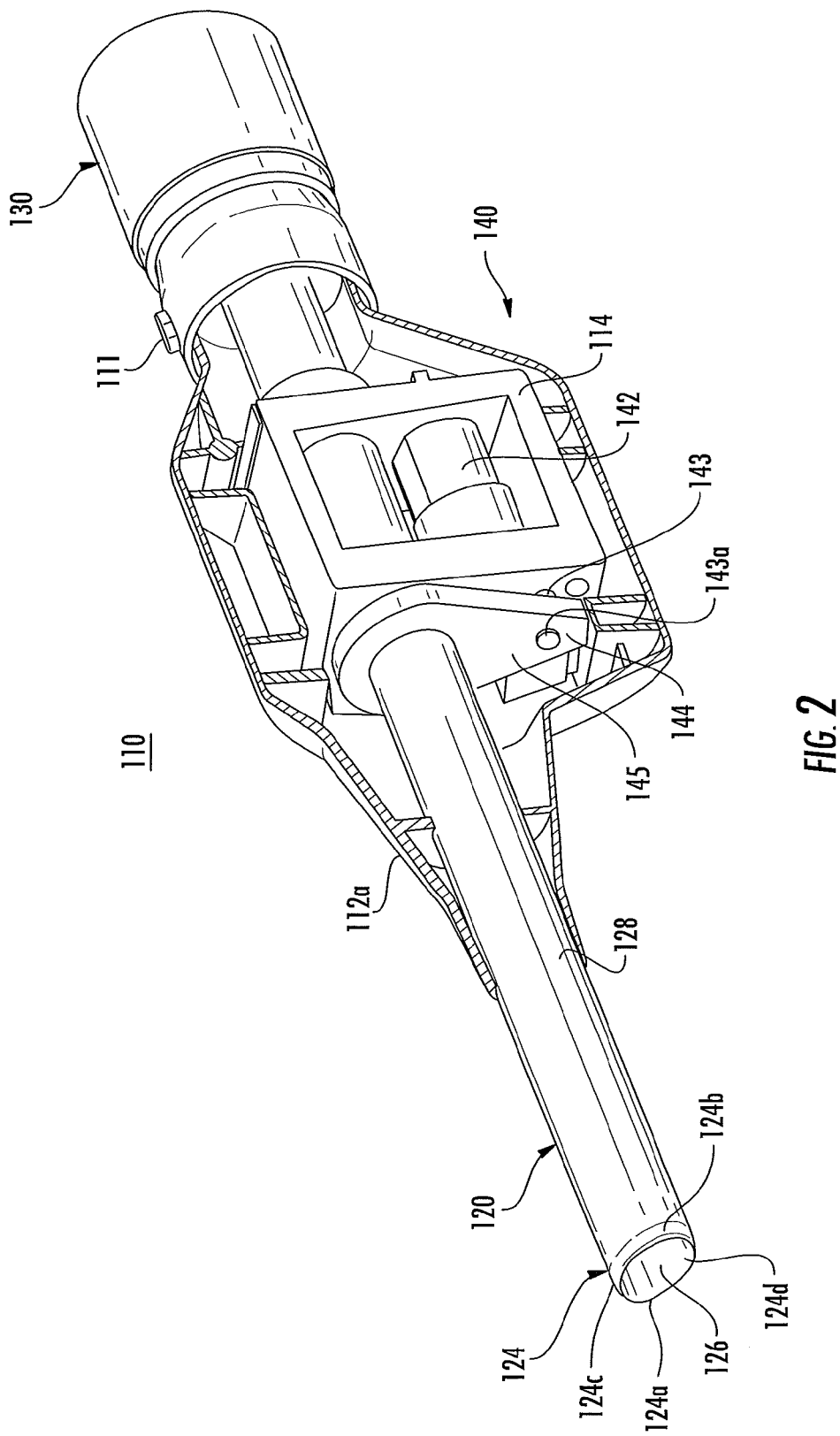
FIG. 2 is a front perspective view of the morcellator of FIG. 1 with a portion of the housing removed to show the internal components thereof.

Referring now to FIGS. 1-5, the oscillating morcellator 110 includes a housing 112, an elongated tube 120, an end cap 130, and an oscillating mechanism 140 (FIG. 2). The housing 112 is formed from first and second body shells 112a, 112b that cooperate to house the oscillating mechanism 140, although other configurations are also contemplated. The first and second body shells 112a, 112b can be engaged or sealed together in any suitable fashion, such as, for example snap-fitting, screwing, welding, and/or gluing. The housing 112 encloses a support or bracket 114.

The elongated tube 120 defines a longitudinal axis A-A and includes a distal end 124, an outer surface 128, and a lumen 126 defined therethrough. The elongated tube 120 extends through the housing 112 and couples to the oscillating mechanism 140 to rotate the elongated tube 120 relative to the housing 112, as detailed below. The distal end 124 of the elongated tube 120 extends distally from the housing 112. The distal end 124 can be sharpened at select locations to form opposed blade sections 124a, 124b (FIG. 2). The distal end 124 can also include blunt sections 124c, 124d. The blunt sections 124c, 124d are designed in a manner to cause the distal end 124 to skive along the surface of tissue rather than plunge directly through tissue. It will be appreciated that blunt sections 124c, 124d will not be damaged by contacting portions of the grasper 150 inserted through lumen 126 to grasp tissue, as detailed below. Other suitable configurations are also contemplated, e.g., sharpening the entire distal end 124, providing greater or fewer blade sections 124a, 124b, etc. The distal end 124 of the morcellator 110 is disposed at an angle θ relative to a plane orthogonal to the longitudinal axis A-A as shown in FIG. 1A. The angle θ may be any suitable angle between 0 degrees and 90 degrees.

The oscillating mechanism 140 includes a motor 142, a cam 143, and a connecting member 144. The motor 142 is mounted within the housing 112 such that the motor 142 and the housing 112 are substantially fixed relative to each other. More specifically, the motor 142 is mounted to the bracket 114. The motor 142 is mounted parallel to the longitudinal axis A-A of the elongated tube 120. The cam 143 is operatively associated with the motor 142 and configured to cooperate with the rotation of the motor 142. The oscillating mechanism 140 can include a proximal collar 147 positioned about the elongated tube 120 to prevent the elongated tube 120 from passing entirely through the bracket 114.

As shown, the cam 143 is directly coupled to the motor 142 such that the cam 143 has a radial velocity equal to the motor 142; however, it is also contemplated that a transmission (not shown) can be positioned between the cam 143 and the motor 142 such that the cam 143 rotates at a radial velocity different than the motor 142. The cam 143 is a disc and includes a cam pin 143a extending distally from and fixed to the surface of the cam 143 near the circumference of the cam 143. The connecting member 144 is fixed about the outer surface 128 of the elongated tube 120 and includes a cam slot 145. The cam slot 145 is sized and configured to receive the cam pin 143a. As the cam 143 rotates the cam pin 143a, the cam pin 143a engages the cam slot 145 to oscillate the connecting member 144 such that the elongated tube 120 oscillates about the longitudinal axis A-A of the elongated tube 120. The oscillating mechanism 140 is configured to oscillate the elongated tube 120 in the range of about 200 to about 1000 cycles per minute (cpm); however, it is contemplated that the oscillating mechanism 140 may be configured to oscillate the elongated tube 120 at higher or lower cpms. The oscillating mechanism 140 is further configured to oscillate the elongated tube 120 approximately 30° about the longitudinal axis A-A; however, it is contemplated that the oscillating mechanism 140 be configured to oscillate the elongated tube 120 to a greater or lesser degree. The motor 142 is mounted perpendicular to the longitudinal axis A-A of the elongated tube 120, while the cam 143 operates in a cam slot 145 that is parallel to the longitudinal axis A-A of the elongated tube 120, although other configurations are also contemplated.

Figure 6:
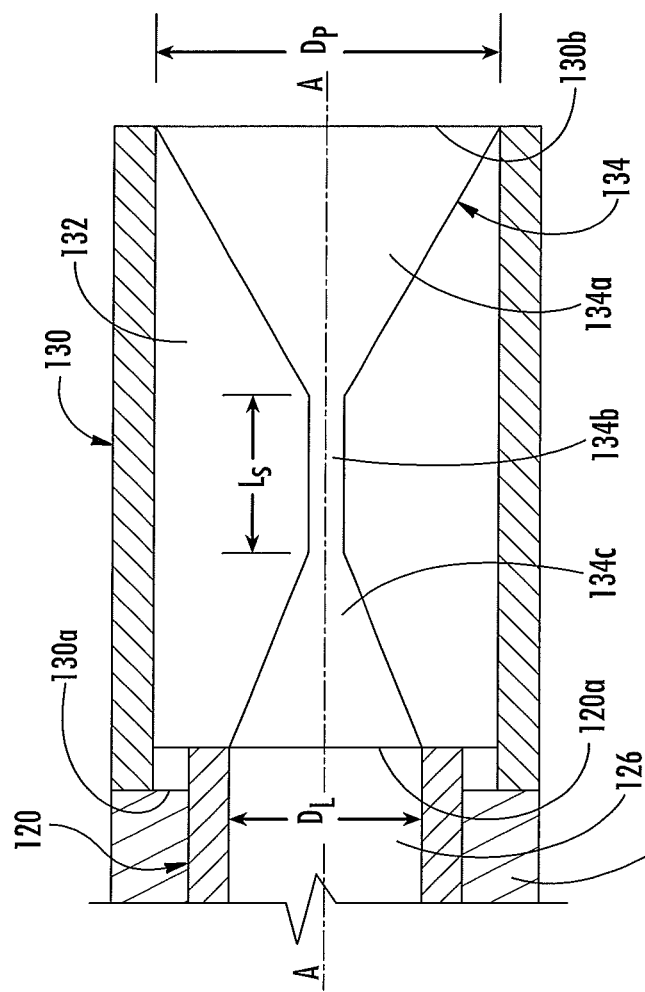
FIG. 6 is a longitudinal cross-sectional view of the morcellator of FIG. 1 including an end cap in accordance with the present disclosure.

Referring to FIGS. 1 and 6, the end cap 130 couples to a proximal end of the housing 112 and includes distal and proximal ends 130a, 130b. The distal and proximal ends 130a, 130b define a keyed passage 132 therebetween. The keyed passage 132 is longitudinally aligned with the longitudinal axis A-A of the elongated tube 120. The distal end 130a of the end cap 130 is disposed about or adjacent to a proximal end 120a of the elongated tube 120. The keyed passage 132 includes a pair of aligning structures or keyways 134 cut into the inner surface of end cap 130. Each keyway 134 opposes the other keyway 134 and is substantially similar to the other keyway 134, as such the structure of the pair of keyways will be described in the singular below. It is also contemplated that keyed passage 132 may only include a single keyway 134 or a plurality of pairs of opposed keyways 134. The keyed passage 132 defines a passage diameter $D_p$.

The keyway 134 includes a first section 134a, a second section 134b, and a third section 134c. The first section 134a is positioned proximal to the second section 134b and the second section 134b is positioned proximal to the third section 134c. The first section 134a tapers from a first dimension, e.g., the passage diameter $D_p$, adjacent the proximal end 130b of the end cap 130 to a second dimension adjacent second section 134b. The second section 134b is substantially constant in diameter along a section length $L_s$ thereof having a dimension substantially equal to the second dimension of the first section 134a. The third section 134c has a dimension substantially equal to the second dimension adjacent the second section 134b and tapers to a third dimension, e.g., a lumen diameter DL of the lumen 126, larger than the second dimension near the proximal end 120a of the elongated tube 120. The rate of the taper of the first section 134a and the third section 134c may be constant or variable along the length thereof.

Referring back to FIG. 1, the grasper 150 includes a grasping end 152, a handle assembly 158, a tubular member 159, and a keyed collar 160. Grasping end 152 is positioned adjacent the distal end of the tubular member 159 and is configured to grasp tissue as detailed below. Grasping end 152 includes first and second jaws 154, 156 moveable relative to one another between an open position and a closed position. The handle assembly 158 is positioned adjacent the proximal end of the tubular member 159 and is operatively associated with the grasping end 152 to move the first and second jaws 154, 156 between the open and closed positions. The grasping end 152 of the grasper 150 is configured to be inserted through the keyed passage 132 of the end cap 130 and through the lumen 126 of the elongated tube 120. In the closed position of the grasping end 152, the first and second jaws 154, 156 are disposed within the lumen diameter DL of the lumen 126. In the open position of the grasping end 152, a portion of at least one of the first and second jaws 154, 156 may be disposed outside of the lumen diameter DL such that the portion of one of the first and second jaws 154, 156 may contact the distal end 124 of the elongated tube 120 as detailed below.

Figure 7:
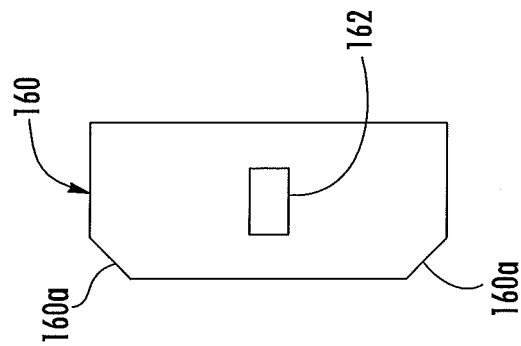
FIG. 7 is a top view of a collar of the grasper of FIG. 1 in accordance with the present disclosure for use with the end cap of FIG. 6.

With additional reference to FIG. 7, the keyed collar 160 is disposed about tubular member 159 and operatively associated with the grasping end 152 such that the grasping end 152 cooperates with the rotation of the keyed collar 160. The keyed collar 160 has an outer diameter slightly smaller than the passage diameter $D_p$ such that the keyed collar 160 is slidably receivable within the keyed passage 132 of the end cap 130 to substantially align the tubular member 159 with the longitudinal axis A-A of the elongated tube 120. It is contemplated that the distal end of the keyed collar 160 include a chamfer 160a to assist in inserting the keyed collar 160 into the keyed passage 132. The keyed collar 160 further includes a key 162 affixed to the outer surface of keyed collar 160. The key 162 is configured be received within keyway 134 of the end cap 130 to radially align the keyed collar 160 with morcellator 110 such that the first and second jaws 154, 156 of the grasping end 152 are aligned with desired sections of the distal end 124 of the elongated tube 120 as detailed below. It is contemplated that keyed collar 160 includes more than one key 162 and that each key 162 be configured to be received within a respective keyway 134 of the end cap 130. As shown, the key 162 is rectangular; however, it is contemplated that the key 162 may have other shapes, e.g., diamond, triangular, cylindrical, etc. In some embodiments, rather than providing a keyed collar 160, the outer diameter of the tubular member 159 is slightly smaller than the lumen diameter DL to longitudinally align the tubular member 159 with the longitudinal axis A-A of the elongated tube 120 and the key 162 is affixed to the outer surface of the tubular member 159.

In some embodiments, the grasper 150 further includes one or more distal collars 166 disposed about the outer surface of the tubular member 159. The distal collar 166 is positioned distal to the keyed collar 160. The outer diameter of the distal collar 166 is slightly smaller than the lumen diameter DL such that the distal collar 166 is slidably receivable within the lumen 126 of the elongated tube 120 to longitudinally align the tubular member 159 with the longitudinal axis A-A of the elongated tube 120. In some embodiments, rather than providing a distal collar 166, the outer diameter of the tubular member 159 is slightly smaller than the lumen diameter DL to longitudinally align the tubular member 159 with the longitudinal axis A-A of the elongated tube 120.

With reference to FIGS. 1-7, the use of the morcellation system 10 is detailed below in accordance with the present disclosure. The morcellator 110 is positioned within a surgical site of a patient. The surgical site can be an incision in a tissue layer or a natural orifice of the body. An access port (not shown) can be inserted through the surgical site with the morcellator 110 being inserted through a port of the access port. The distal end 124 of the elongated tube 120 is positioned within the body of a patient near the tissue to be morcellated but not in contact with other tissue within the body of the patient. The grasping end 152 of the grasper 150 is inserted through the keyed passage 132 of the end cap 130 and the lumen 126 of the elongated tube 120 of the morcellator while in the closed position. The key 162 of the keyed collar 160 engages the taper of the first section 134a of the keyway 134 to urge the key 162 to a position capable of passing through the second section 134b of the keyway 134. As the grasping end 152 exits or emerges from the distal end 124 of the elongated tube 120, the key 162 is positioned within second section 134b of keyway 134 inhibiting the rotation of grasper 150 relative to the morcellator 110 such that the first and second jaws 154, 156 of the grasping end 152 are aligned with designated sections of the distal end 124 of the elongated tube 120, e.g., the blunt sections 124c, 124d of the distal end 124. When the grasping end 152 is positioned distally of the distal end 124 of the elongated tube 120, such that the jaws 154, 156 can no longer contact the distal end 124 of the elongated tube 120, the key 162 transitions from second section 134b to the third section 134c permitting rotation of the grasper 150 relative to the morcellator 110. The key 162 and/or the keyed collar 160 may further act as a stop to inhibit the handle assembly 158 from engaging the end cap 130 or passing through the end cap 130.

When the grasping end 152 of the grasper 150 protrudes from the distal end 124 of the elongated tube 120, the handle assembly 158 of the grasper 150 is manipulated to transition the first and second jaws 154, 156 between the open and closed positions to grasp the tissue to be morcellated. The grasper 150 is then withdrawn into the elongated tube 120 to bring the tissue to be morcellated into contact with the distal end 124 of the elongated tube 120. It will be appreciated that when in the open position, depending on the depth of insertion of the grasping end 152 through elongated tube 120, portions of the first and second jaws 154, 156 may contact the distal end 124 of the elongated tube 120. When the grasping end 152 is positioned relative to the distal end 124 of the elongated tube 120 such that portions of the first and second jaws 154, 156 contact distal end 124 when in the open position, the key 162 of the collar 160 is positioned within the second section 134b of the keyway 134 to align the first and second jaws 154, 156 with desired sections, e.g., blunt sections 124c, 124d, of the distal end 124. It will be appreciated that the section length $L_s$ of the second section 134b is equal to the depth distance length range of the grasping end 152 at which the first and second jaws 154, 156 contact the distal end 124 when the grasping end 152 is in the open position.

When the tissue to be morcellated is in contact with the distal end 124 of elongated tube 120, the oscillation mechanism 140 is activated such that the elongated tube 120 oscillates to cut through the tissue in contact with the distal end 124. An activation button 111 (FIG. 1) can be depressed to activate the oscillation mechanism 140. As the distal end 124 oscillates, blade sections 124a, 124b cut through the tissue while blunt sections 124c, 124d guide distal end 124 over the surface of the tissue to skive material from the outer surface of the tissue. The distal end 124 is configured to skive tissue from the surface to inhibit the distal end 124 from plunging through the tissue. By skiving layers from the surface of the tissue, long strips of tissue can be removed as the tissue is rotated relative to the morcellator 110 to continually feed tissue to the morcellator 110. The morcellated tissue can be removed through the end cap 130 with the grasper 150.

In some embodiments, the lumen 126 and/or the passage 132 include a seal (not shown) configured to maintain insufflation and/or patronal pressure during surgical procedures. The seal can also be configured to conform to the grasper 150 and/or skived strip of tissue passing through the seal.

In some embodiments, the end cap 130 may be releasably engagable with the proximal end of the housing 112, e.g., via friction fitting, snap-fitting, etc. Additionally or alternatively, the collar 160 may be releasably engagable about the tubular member 159 of the grasper 150. As such, an appropriate end cap and collar may be selected for use with a particular oscillating morcellator and grasper combination and/or depending on the particular procedure to be performed. For example, various different end caps may be provided for use with graspers having jaws of different lengths.

Figure 9:
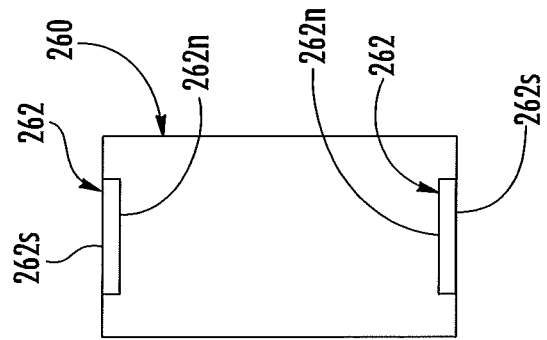
FIG. 9 is a side view of another collar in accordance with the present disclosure for use with the end cap of FIG. 8.
Figure 8:
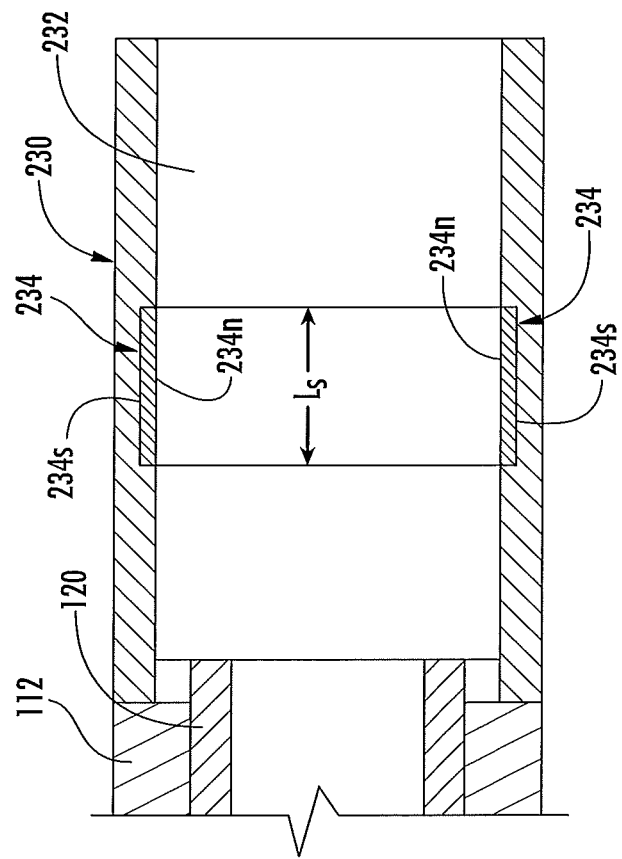
FIG. 8 is a longitudinal cross-sectional view of the morcellator of FIG. 1 including another end cap in accordance with the present disclosure.

Referring to FIGS. 8 and 9, another exemplary embodiment of an end cap 230 and a keyed collar 260 are provided in accordance with the present disclosure. The end cap 230 and the keyed collar 260 are similar to the end cap 130 and the collar 160, respectively, described above, as such only the differences will be detailed below.

The end cap 230 includes a pair of aligning structures or cap magnets 234 disposed on or with a sidewall of a passage 232. Each cap magnet 234 is aligned with one pole $234_n$, representing the north pole of each cap magnet 234, facing towards the passage 232 and one pole $234_s$, representing the south pole of each cap magnet 234, facing away from the passage 232. As shown, each cap magnet 234 is aligned with pole $234_n$ facing the passage 232; however, it is also contemplated that each magnet 234 be aligned with pole $234_s$ facing passage 232. In some embodiments, one of the pair of cap magnets 234 is aligned with pole $234_n$ facing the passage 232 and the other of the pair cap magnets 234 is aligned with pole $234_s$ facing the passage 232. Each cap magnet 234 has a length $L_s$ substantially similar to the section length $L_s$ of the second section 134b described above (FIG. 6).

The keyed collar 260 includes a pair of keys or collar magnets 262 disposed on or within the outer surface of the keyed collar 260. Each collar magnet 262 is aligned with a pole $262_s$, representing the south pole of each collar magnet 262, facing outward and a pole $262_n$, representing the south pole of each collar magnet 262, facing inward. Each collar magnet 262 is configured to cooperate with one or both of the cap magnets 234 when the keyed collar 260 is inserted into the passage 232 of the end cap 230 as detailed below.

With reference to FIGS. 1, 8, and 9, when the grasper 150 is inserted into the end cap 230 with the keyed collar 260 coupled to the tubular member 159, the collar magnets 262 cooperate with cap magnets 234 to align the first and second jaws 154, 156 with the distal end 124 of the elongated tube 120. More specifically, when the collar 260 is received within the end cap 230, each pole $262_s$ of the collar magnets 262 is attracted to a pole $234_n$ of a respective cap magnet 234 to align the first and second jaws 154, 156 with the distal end 124 of the elongated tube 120. In embodiments where other configurations are provided, e.g., where the poles $234_s$ of the cap magnets 234 are facing the passage 232 and the poles $262_n$ of the collar magnets 262 are facing outward, attraction between the magnets 234, 262 similarly aligns the first and second jaws 154, 156 with the distal end 124 of the elongated tube 120.

In other embodiments, each cap magnet 234 is aligned with the pole $234_n$ facing passage 232 and each collar magnet 262 is aligned with the pole $234_n$ facing outward. In such embodiments, when the collar 260 is received within the end cap 230, each pole $262_n$ of the collar magnets 262 is repelled by the pole $234_n$ of each cap magnet 234 to align the first and second jaws 154, 156 with the distal end 124 of the elongated tube 120. It is also contemplated that the alignment of the magnets 234, 262 may be reversed such that alignment by repelling of magnets 234, 262 may similarly be effected.

In yet other embodiments, a first cap magnet 234*a* is aligned with the pole 234$_n$ facing passage 232 and a second cap magnet 234*b* is aligned with pole 234$_s$ facing passage 232 and a first collar magnet 262*a* is aligned with the pole 262$_s$ facing outward and a second collar magnet 262*b* is aligned with the pole 262$_n$ facing outward. In such embodiments, when the collar 260 is received within the end cap 230, the pole 262$_s$ of the first collar magnet 262*a* is attracted to the pole 234$_n$ of the first cap magnet 234*a* and repelled by the pole 234$_s$ of the second cap magnet 234*b* and the pole 262$_n$ of the second collar magnet 262*b* is attracted to the pole 234*s* of the second cap magnet 234*b* and is repelled by the pole 234$_n$ of the first cap magnet 234*a* to align the first and second jaws 154, 156 with the distal end 124 of the elongated tube 120. The reverse configuration for achieving a similar result is also contemplated.

Figure 10:
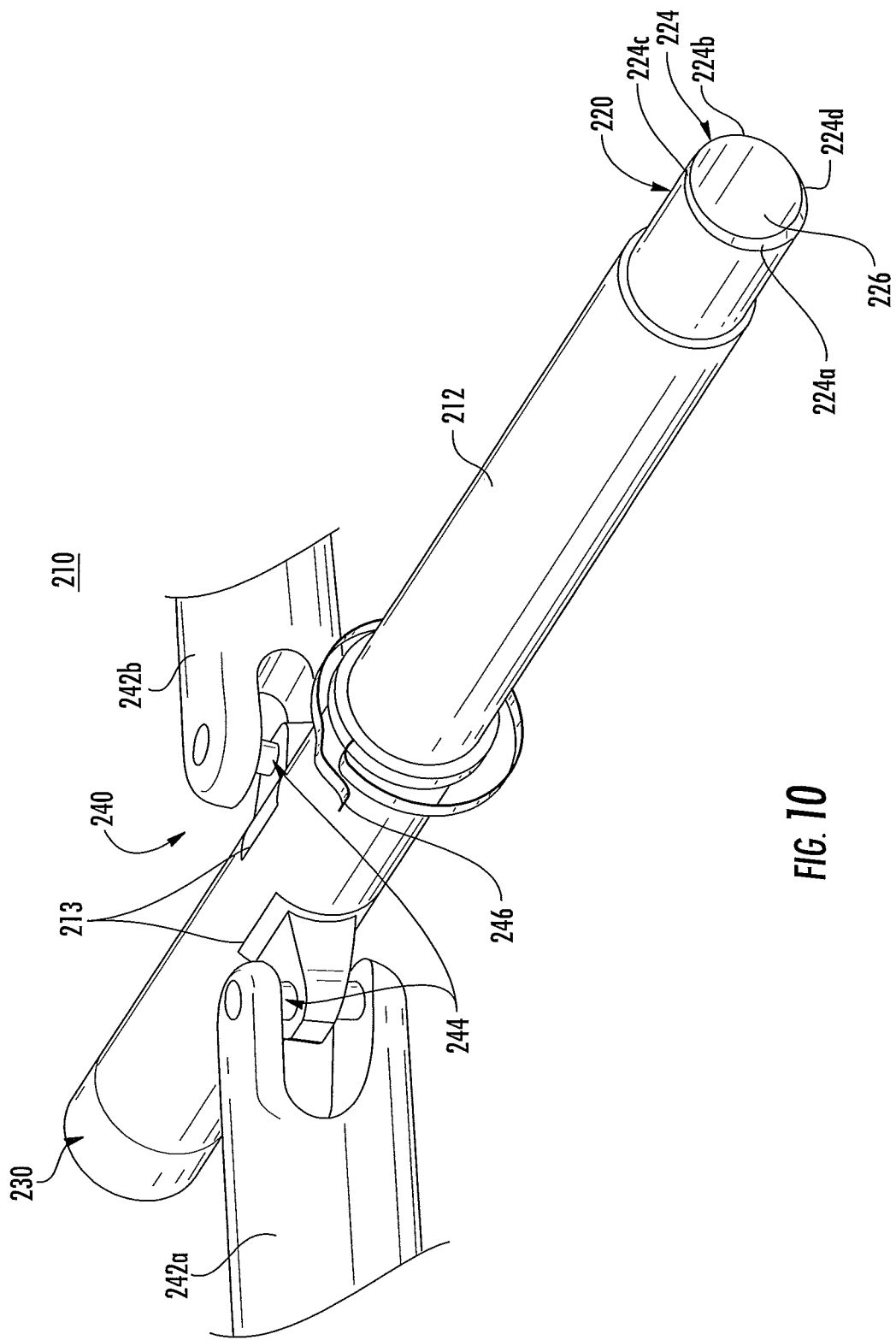
FIG. 10 is a front perspective view of another morcellator in accordance with the present disclosure.

Referring now to FIG. 10, another oscillating morcellator 210 is provided in accordance with the present disclosure incorporating a housing 212, an elongated tube or metal insert 220, an end cap 230, and an oscillating mechanism 240. Housing 212 is constructed from a non-conductive and non-magnetic material such as a plastic. Housing 212 can include openings 213 in a proximal portion. The end cap 230 is coupled to the housing such that a proximal end 220*a* of the metal insert 220 is received within a passage 232 of the end cap 230.

Metal insert 220 has a proximal end (not shown), a distal end 224, and a lumen 226 extending therebetween. Portions of distal end 224 can be sharpened to create blade sections 224*a*, 224*b*. Similar to distal end 124 of elongated tube 120, described above, portions of distal end 224 can be left blunt to form blunt sections 224*c*, 224*d* that enhance the skiving properties of metal insert 220 and provide a contact surface for a tenaculum.

Oscillating mechanism 240 includes solenoids 242*a*, 242*b*, magnets 244, and spring assembly 246. Solenoids 242*a*, 242*b* are positioned about magnets 244 such that as energy is passed through solenoids 242*a*, 242*b* each produces a magnetic field that acts on magnets 244 as described in detail below. Magnets 244 are fixed to metal insert 220 and are configured to rotate metal insert 220 in response to the magnetic fields produced by solenoids 242*a*, 242*b*. Magnets 244 can pass through openings 213 in the proximal portion of housing 212 and affix to metal insert 220. Oscillating mechanism 240 is configured to oscillate elongated tube 220 in the range of about 200 to about 1000 cycles per minute (cpm); however, it is contemplated that oscillating mechanism 240 may be configured to oscillate elongated tube 220 at higher or lower cpms. Oscillating mechanism 240 is further configured to oscillate elongated tube 220 approximately 30° about the longitudinal axis; however, it is contemplated that oscillating mechanism 240 be configured to oscillate elongated tube 220 to a greater or lesser degree.

In some embodiments, oscillating mechanism 240 includes a spring assembly 246 operatively associated with metal insert 220. Spring assembly 246 has a stiffness such that cutting blade operates at or near a natural frequency controlled by the rotational inertia of metal insert 220 and the strain energy of the spring. The harmonic drive of the oscillating mechanism can be matched or tuned to the natural frequency. It will be appreciated that oscillating mechanism 140, described above, can include a similar spring assembly.

In some embodiments, the end cap 130 (FIG. 1) may be used as an alternative to end cap 230 with morcellator 210. Morcellator 210 operates similar to morcellator 110 described above, as such the operation of morcellator 210 will not be detailed below for reasons of brevity.

In accordance with the present disclosure, a morcellation kit is provided including a morcellation system, e.g., morcellation system 10. The morcellator in the morcellation kit may be any one of or combination of morcellators 110 and 210 described above including one or more of end caps 130, 230. The grasper of the morcellation kit may be the grasper 150 any one of or combination of collars 130, 166, and 260. The morcellation kit may include a specimen retrieval apparatus (not shown) configured to encapsulate the tissue to be morcellated and to facilitate sealed removal of the tissue. An example of such a surgical retrieval apparatus is disclosed in U.S. patent application Ser. No. 13/713,075 filed Dec. 13, 2012, the contents of which are hereby incorporated by reference in their entirety. In use, the surgical retrieval apparatus is configured to be inserted within the surgical site and the specimen retrieval bag deployed to encapsulate the tissue to be morcellated to substantially inhibit portions of the tissue to be morcellated from contacting and/or contaminating other tissue. The distal end of the morcellator is configured to be inserted into the specimen retrieval bag to morcellate the tissue encapsulated therein. The distal end of the morcellator and/or the specimen retrieval bag is configured to inhibit the morcellator from cutting through the specimen retrieval bag. The grasper is configured to feed tissue to the distal end of the morcellator, such as a tenaculum or surgical grasper.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A morcellation system comprising:
   a morcellator including:
   a housing;
   an elongated tube extending distally from the housing, the elongated tube defining a longitudinal axis and a lumen therethrough, a distal end of the elongated tube including at least one blade section configured to cut tissue;
   an oscillating mechanism configured to oscillate the elongated tube about the longitudinal axis;
   an end cap coupled to the proximal end of the housing and configured to receive a proximal end of the elongated tube, the end cap defining a passage disposed about the longitudinal axis of the elongated tube; and
   an aligning structure disposed in the passage of the end cap; and
   a grasper including:
   a tubular member having a proximal end and a distal end;
   a grasping end positioned adjacent the distal end of the tubular member and having first and second jaws moveable relative to one another;

a handle assembly positioned adjacent the proximal end of the tubular member and operatively associated with the grasping end; and a keyed collar disposed about the tubular member between the proximal and distal ends thereof, the keyed collar including a key configured to cooperate with the aligning structure of the end cap to align the first and second jaws relative to the distal end of the elongated tube.

2. The morcellation system of claim 1, wherein the at least one blade section is disposed at an angle relative to a plane orthogonal to the longitudinal axis.

3. The morcellation system of claim 1, wherein the oscillating mechanism is configured to mechanically drive the elongated tube to oscillate.

4. The morcellation system of claim 3, wherein the oscillating mechanism includes a motor, a disc shaped cam, and a connecting member, the cam coupled to the motor and having a distally extending cam pin affixed near the outer circumference of the cam, the connecting member fixed to the outer surface of the elongated tube and defining a cam slot configured to receive the cam pin such that the cam and the connecting member cooperate to translate rotation of the motor into oscillation of the elongated tube.

5. The morcellation system of claim 1, wherein the oscillating mechanism is configured to electromagnetically drive the elongated tube to oscillate.

6. The morcellation system of claim 5, wherein the oscillation mechanism includes at least one magnet affixed to the elongated tube and at least one solenoid disposed in operable communication with the at least one magnet, the at least one solenoid selectively energizable to generate magnetic fields that act upon that at least one magnet to oscillate the elongated tube.

7. The morcellation system of claim 1, wherein the aligning structure is a keyway, and wherein the key protrudes from the outer surface of the keyed collar.

8. The morcellation system of claim 7, wherein the keyway includes a first section, a second section, and a third section, the first section tapering distally from a first dimension to a second dimension smaller than the first dimension, the second section having a substantially constant dimension equal to the second dimension, and the third section tapering distally from the second dimension to a third dimension greater than the second dimension.

9. The morcellation system of claim 1, wherein the aligning structure is a pair of cap magnets and wherein the key is a pair of collar magnets.

10. A surgical kit, comprising:
a morcellator, including:
a housing;
an elongated tube extending distally from the housing, the elongated tube defining a longitudinal axis and a lumen therethrough, a distal end of the elongated tube configured to cut tissue;
an end cap coupled to a proximal end of the housing and configured to receive a proximal end of the elongated tube, the end cap defining a passage disposed about the longitudinal axis of the elongated tube; and
an aligning structure disposed in the passage of the end cap;
and
a grasper configured to feed tissue to the distal end of the morcellator to facilitate tissue morcellation, the grasper including:
a tubular member having a proximal end and a distal end;
a grasping end positioned adjacent the distal end of the tubular member and having first and second jaws moveable relative to one another;
a handle assembly positioned adjacent the proximal end of the tubular member and operatively associated with the grasping end; and
a keyed collar disposed about the tubular member between the proximal and distal ends thereof, the keyed collar including a key configured to cooperate with the aligning structure of the end cap to align the first and second jaws relative to the distal end of the elongated tube.

11. The kit of claim 10, wherein the morcellator further includes an oscillating mechanism configured to oscillate the elongated tube about the longitudinal axis, the distal end of the elongated tube including opposing blade sections and opposing blunt sections.

12. The kit of claim 11, wherein the oscillating mechanism is configured to electromagnetically drive the elongated tube to oscillate.

13. The kit of claim 11, wherein the oscillating mechanism is configured to mechanically drive the elongated tube to oscillate.

14. The kit of claim 10, wherein the aligning structure is a keyway and the key protrudes from the outer surface of the collar configured to be received within the keyway.

15. The kit of claim 10, wherein the aligning structure is a pair of cap magnets and the key is a pair of collar magnets.

* * * * *